United States Patent [19]

Grau

[11] 4,405,233

[45] Sep. 20, 1983

[54] PHOTO-ELECTRIC APPARATUS FOR TESTING ELECTRICAL CONNECTOR CONTACTS

[75] Inventor: Thomas G. Grau, Mendham Township, Morris County, N.J.

[73] Assignee: Bell Telephone Laboratories, Incorporated, Murray Hill, N.J.

[21] Appl. No.: 156,565

[22] Filed: Jun. 5, 1980

[51] Int. Cl.$^3$ .................... G01N 21/00; G01R 31/04
[52] U.S. Cl. ................. 356/237; 250/223 R; 324/51; 324/73 R; 356/241
[58] Field of Search .............. 356/237, 244, 246, 241; 324/51, 54, 73 R, 73 PC; 209/524, 536, 576; 250/223 R, 223 B; 235/92 V, 92 PK

[56] References Cited

U.S. PATENT DOCUMENTS

| | | | |
|---|---|---|---|
| 3,773,426 | 11/1973 | Mudd | 356/246 X |
| 3,826,923 | 7/1974 | Trimble et al. | 250/223 R X |
| 3,980,180 | 9/1976 | Jamieson | 250/223 R X |
| 4,004,150 | 1/1977 | Natelson | 356/246 |
| 4,066,316 | 1/1978 | Rollings . | |
| 4,241,293 | 12/1980 | Bross | 250/223 R X |
| 4,264,202 | 4/1981 | Gugliotta et al. | 356/241 |
| 4,266,674 | 5/1981 | Bell et al. | 250/223 R X |

FOREIGN PATENT DOCUMENTS 55-142254 11/1980 Japan ..................................... 324/51

Primary Examiner—Gerard R. Strecker
Attorney, Agent, or Firm—W. H. Kamstra

[57] ABSTRACT

Electrical connector testing apparatus for detecting obstructions in the connector contact terminal pin receptacle channels caused by defective receptacle blades (18, 19). A carriage (22) for retaining a connector (20) in an upright position is movable between upper and lower horizontal members (40, 41) of a detection frame (36) to position the contact receptacles (16, 17) row by row between corresponding pairs of light emitting diodes and phototransistors (45, 44) fitted respectively in the horizontal members (40, 41). Light beams generated by the diodes (45) pass unobstructed through properly fitted contact receptacles (16) and are interrupted by receptacles (17) having defective, bent blades. The phototransistors (44) detect the unobstructed light beams and transmit signals indicative of properly fitted receptacles (16) to control circuitry (65), which may conveniently comprise a microprocessor, which may then be programmed to initiate appropriate action for the identification of the defective connector.

8 Claims, 4 Drawing Figures

PHOTO-ELECTRIC APPARATUS FOR TESTING ELECTRICAL CONNECTOR CONTACTS

TECHNICAL FIELD

This invention relates to electrical connector assemblies and more particularly to apparatus for testing such assemblies after fabrication.

BACKGROUND OF THE INVENTION

Electrical connector arrangements for interconnecting the conductors of a multiple conductor cable and the like with the terminal pins of a backplane or other electrical components are well known in the art. One such connector arrangement is described, for example, in the patent of R. W. Rollings, U.S. Pat. No. 4,066,316, issued Jan. 3, 1978, which connector employs as its basic circuit completion element an electrical contact which at one end provides for the piercing of the conductor insulation to reach the conductor. At its other end, the contact has formed thereon a pair of opposing spring blades which present a receptacle for a terminal pin, the blades clasping the pin by opposing spring action when inserted therebetween. Banks of the contacts are fitted into rectangular slots provided therefor in an insulative housing, the front face of which presents corresponding banks of funnel-like capture cones for facilitating the entry of a corresponding array of terminal pins into the contact receptacles. In order to ensure that the receptacle blades are sufficiently separated to admit the pins, each of the housing slots is provided with ribs on its opposing side walls upon which ribs the contact blades ride during their fitting in the connector assembly. The ribs thus slightly separate the receptacle blades against the urging of their closing spring action.

Other connector contact arrangements providing specifically different conductor terminations are also known in the art. Thus, for example, a contact at its conductor terminating end could provide for soldered connections to a printed wiring board rather than to insulated conductors of a cable. Whatever the conductor terminating end of the connector, this invention is chiefly concerned with the contact pin receptacle end and, more particularly, with the problems encountered in their assembly in the connector. The contacts are typically inserted in their respective slots, receptacle end first, from the rear of the connector, the slightly outwardly flared opposing blade ends normally being separated by the side wall ribs of the slots and then riding thereon until the contact is fully inserted. On occasion, however, because of the misalignment or bent blade end, both of the blades may be forced between the top or bottom wall and one side of the slot side wall ribs. Not only is the entry of a terminal pin at the defective receptacle thus blocked, but the full fitting of other pins in the connector may be prevented as well.

Visual inspection of the connectors for defectively fitted contacts is not only time consuming but, because of their extremely small dimensions (adapted in a typical case to receive pins of 0.025 inch to a side), may also be less than completely reliable. It is thus an objective of this invention to provide new and novel apparatus for facilitating the inspection of the contacts of electrical connectors for proper fit. Specifically, this invention concerns apparatus for performing this inspection automatically for also significantly decreasing inspection time.

SUMMARY OF THE INVENTION

The operation of an inspection apparatus according to this invention for achieving the foregoing objectives is based on the fact that when a contact has been properly fitted in its connector slot, an unobstructed channel is presented from the front face of the connector to its rear between the receptacle blades riding on either side of the slot guide rib. This channel is blocked by one or the other of the receptacle blades when both are trapped on one side of the rib. In accordance with the invention, the blocked and unblocked state of the channel is advantageously employed to control a light beam directed therethrough. A connector to be inspected is retained on a carriage which is adapted to be moved between a row of light emitting diodes (LEDs) and a corresponding row of phototransistors, the rows of both corresponding to the rows of connector terminal pin receptacles. Circuitry associated with the phototransistors detects when one or more of the light beams is interrupted by a defective contact receptacle as the connector is moved row by row under the beams. An additional LED-phototransistor pair is employed to index the connector receptacle rows for identification by means of an aperture provided for each connector row in the carriage as the successive connector rows are passed therebetween. These operations may advantageously be accomplished under microprocessor control, and signals generated by uninterrupted light beams may be employed, also under such control, in any suitable manner to identify the connector revealed as having a defective contact receptacle.

BRIEF DESCRIPTION OF THE DRAWING

The features of an electrical connector contact testing apparatus according to this invention will be better understood from a consideration of the detailed description of the organization and operation of one illustrative embodiment thereof which follows when taken in conjunction with the accompanying drawing in which.

DETAILED DESCRIPTION

Figure 1:
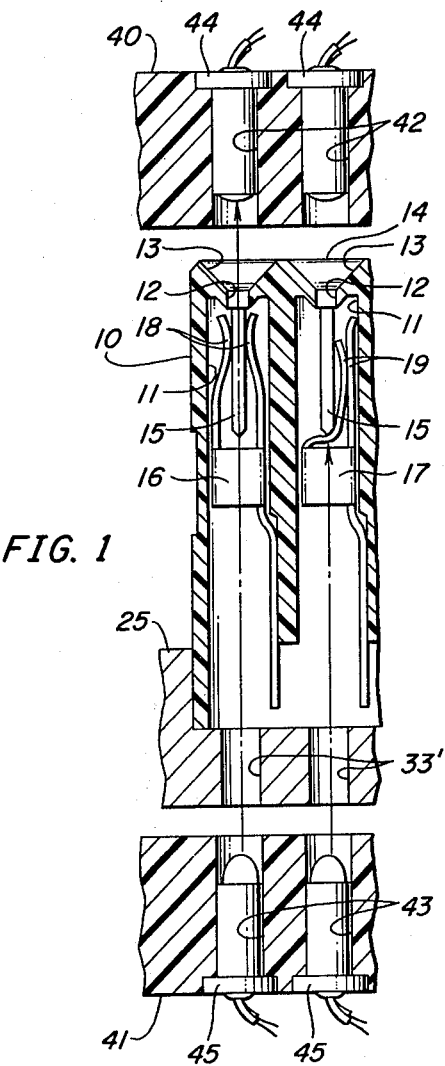
FIG. 1 is an enlarged cross-sectional view of a portion of a connector assembly having a properly and an improperly fitted contact receptacle, the figure also demonstrating the interruption of a light beam by the latter receptacle.

The problem to which the testing apparatus of the invention is directed is demonstrated in FIG. 1 where a sectional portion of a typical electrical connector housing 10 is shown. A pair of slots 11 is provided in the housing which opens via apertures 12 to capture cones 13 presented on the front face 14 of connector 10. Each of the side walls of slots 11 has formed thereon at midpoint a rib 15 extending from aperture 12 rearward for a length of slot 11, ribs 15 terminating at the rear in beveled ends. Shown as already fitted into slots 11 are contacts 16 and 17, the receptacle ends of which are presented by pairs of opposing blades 18 and 19, respectively. The rearward termination of contacts 16 and 17 are not important for an understanding of the invention and accordingly need not be considered. When contacts 16 and 17 are fitted in slots 11, the closing spring action of blades pairs 18 and 19 normally causes their slightly outwardly flared ends to be separated by the beveled ends of ribs 15, the blades then riding on opposite sides of ribs 15 to present suitably dimensioned receptacles for the admission of backplane terminal pins. A properly separated blade pair by ribs 15 is shown in FIG. 1 in connection with contact 16. If, on the other hand, for any reason such as misalignment of the blades or a bent blade end, a blade pair is not forced open by a rib 15, both blades may be trapped to one side of the rib and admission of a terminal pin is effectively prevented. This condition is shown in the case of blade pair 19. As a result, as shown in FIG. 1, before the admission of a terminal pin, a clear and unobstructed channel is presented from the front face 14 of connector housing 10 to its open rear between blade pair 18. This channel is blocked by the deformed blade of blade pair 19.

Figure 2:
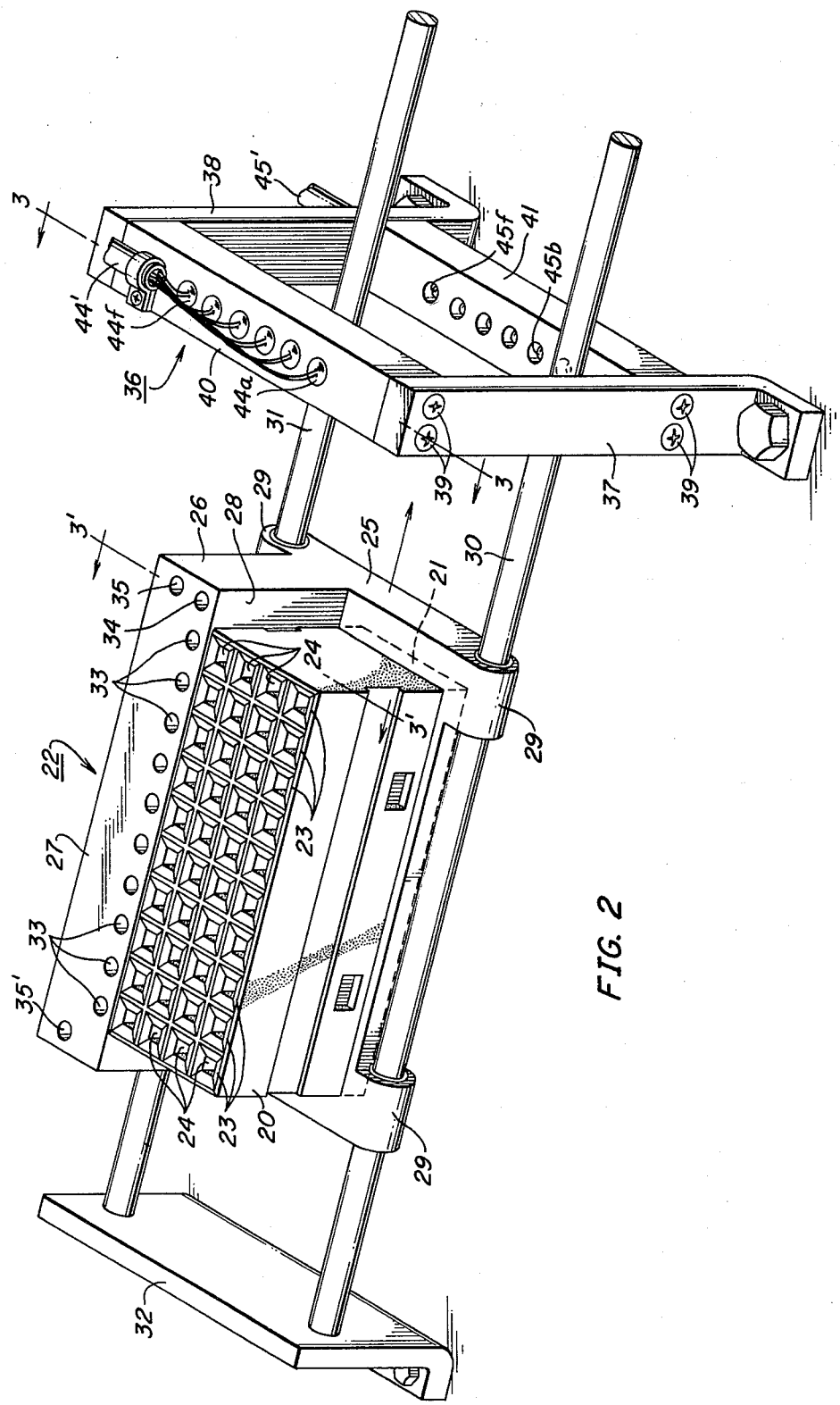
FIG. 2 is a perspective view of the mechanical aspects of an illustrative inspection apparatus according to the invention, its mounting base being assumed and not shown.

With this background of the defect for which the contemplated electrical connector is to be inspected in mind, apparatus according to the invention for performing the inspection and testing may now be considered. In the perspective view of FIG. 2, a connector housing 20 of the general character of the housing described in the aforementioned Rollings patent is shown as supported within a rectangular recess 21 provided therefor in a carriage 22. The upwardly facing front face of housing 20 presents a plurality of rows 23 of four capture cones 24 each opening to the contact receptacles within housing 20. Carriage 22 comprises a base 25 in which a recess 21 is formed and an upright 26 presenting an upper face 27 substantially even with the front face of connector housing 20. The facing side wall 28 of upright 26 extends downward into recess 21 and provides back alignment support for one outer wall of housing 20. Carriage 22 is provided at each corner of its rectangular base 25 with an inwardly extending lug 29 each lug being drilled for slidable movement on a pair of parallel rails 30 and 31. Rails 30 and 31 are fixedly mounted with respect to any slidable base or platform 32' shown only partially in FIG. 3 by means of appropriate mounting members 32, only one of which is shown.

Figure 3:
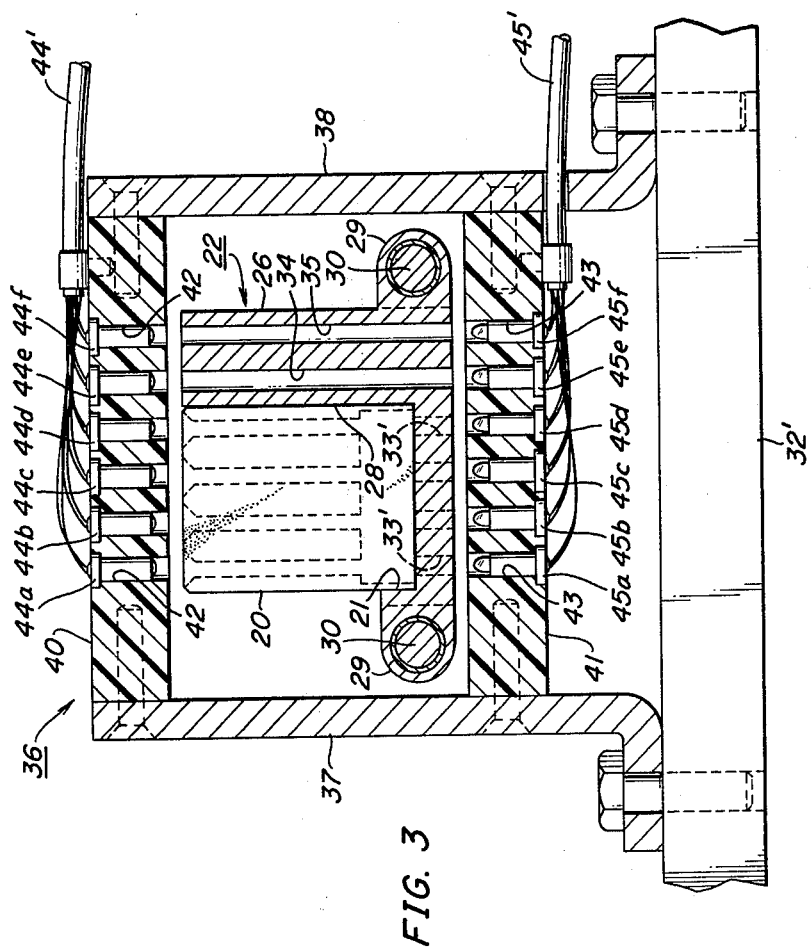
FIG. 3 is an enlarged section view of the apparatus of FIG. 2 taken along the lines 3—3 and 3'—3', the connector and its carriage being assumed as being in a position immediately prior to the testing of a first row of its receptacle rows.

Upright 26 has drilled therethrough from its upper face a plurality of apertures 33 corresponding to and in alignment with, the rows 23 of capture cones 24 of housing 20. Base 25 also has a rectangular array of holes 33' provided therein as shown in dashed outline in FIG. 3 to correspond with the rectangular array of channels extending through connector housing 20 downward from capture cones 24. An additional pair of apertures 34 and 35 are provided in upright 26 preceding the first row 23 of capture cones 24 and a final aperture 35' is provided in upright 26 in alignment with aperture 35 and following the last row of rows 23 of capture cones 24 of housing 20. Carriage 22 is laterally slidable on rails 30 and 31 through a rectangular inspection frame 36 through which the rails extend, frame 36 being shown in detail in the sectional view of FIG. 3. The frame comprises a pair of side uprights 37 and 38 having mounted therebetween in any convenient manner such as by screw means 39, upper and lower horizontal members 40 and 41. Frame 36 is maintained in a fixed relationship with mounting members 32 and thereby with rails 30 and 31 by its mounting on the same base of platform 32'. Members 40 and 41 have drilled therein a plurality of oppositely aligned holes 42 and 43, respectively, spaced to correspond with the contact receptacle capture cones 24 of connector housing 20 and apertures 34 and 35 of carriage 22. Holes 42 of upper member 40 have respectively fitted therein a plurality of phototransistors 44a through 44f. A corresponding plurality of light emitting diodes 45a through 45f are fitted respectively in lower member 41. As represented by arrows in FIG. 1 and generally in FIG. 3, a plurality of corresponding channel a through f are thus presented between diodes 45 and phototransistors 44 through connector housing 20 and carriage upright 25. The sectional view of FIG. 3 shows carriage 22 moved along rails 30 and 31 to a position where its apertures 34 and 35 are directly between and in alignment with phototransistors 44e and 44f and diodes 45e and 45f, respectively. Signal and power conducting paths for the phototransistors and diodes are provided by cables 44' and 45', respectively, extending to control and detection circuitry which may now be considered with particular reference to FIG. 4.

Figure 4:
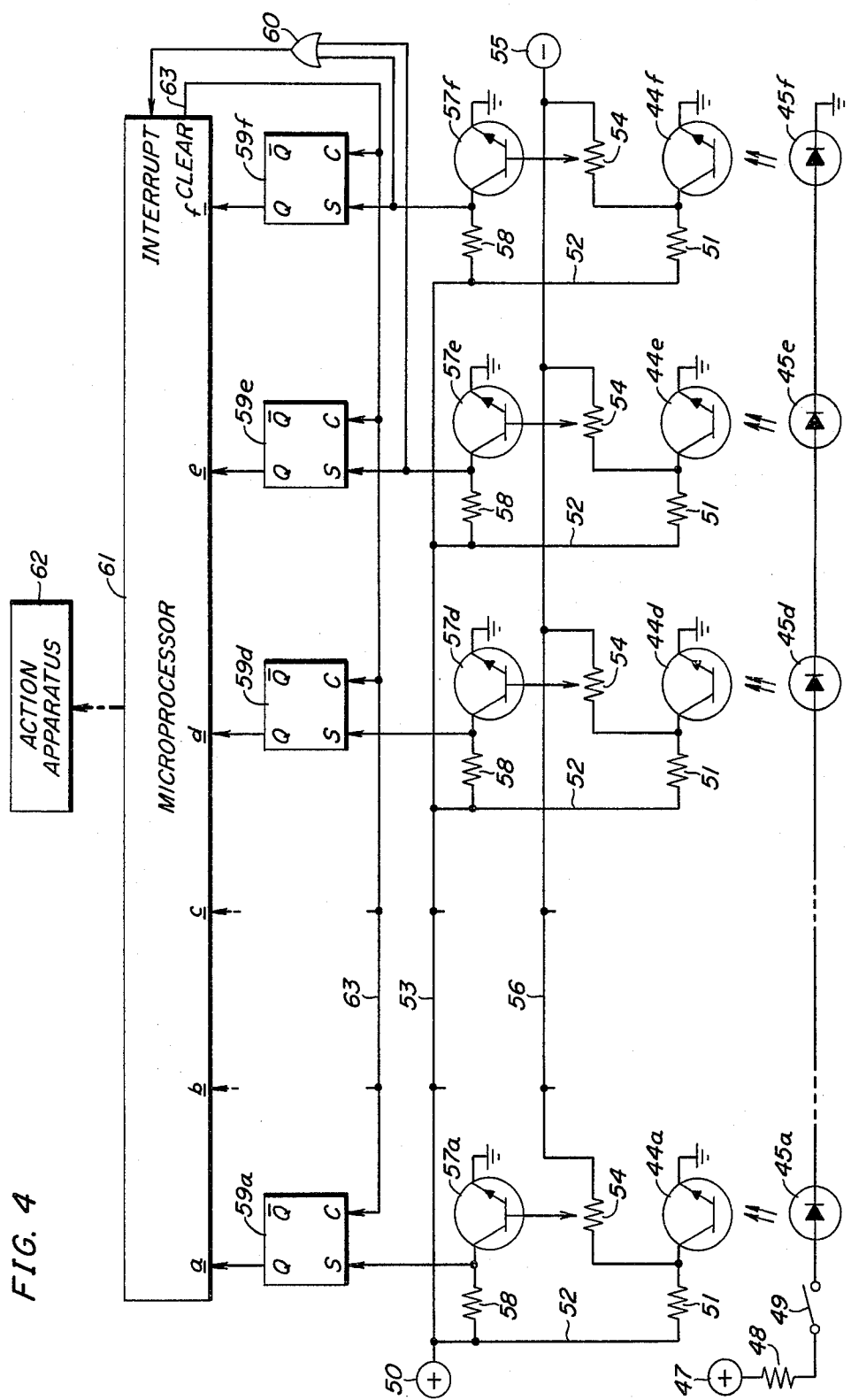
FIG. 4 is a schematic diagram of illustrative circuitry for controlling the apparatus of this invention and for responding to the signals generated thereby.

Representative ones of light emitting diodes 45a through 45f are shown as serially connected between a source of positive potential 47 and ground via current limiting resistor 48 and a make switch 49. The phototransistors of FIG. 3, representative ones 44a, . . . 44d, 44e, and 44f of which are shown in FIG. 4, are connected at the emitters to ground and at the collectors to a source of positive potential 50 via resistors 51, respective conductors 52, and a conductor 53. The collectors of phototransistors 44 are also connected through potentiometers 54 to a source of negative potential 55 via a conductor 56. A plurality of NPN transistors 57a through 57f are connected at the bases to the collectors of corresponding phototransistors 44a through 44f, respectively, via the variable terminals of potentiometers 54. The emitters and collectors of transistors 57a through 57f are connected between ground and potential source 50 via resistors 58, conductors 52, and conductor 53. The collectors of transistors 57a through 57d are connected, respectively to the Set inputs of flip-flops 59a through 59d, only the latter representative ones being shown in the figure. The collectors of transistors 57e and 57f are connected to the input terminals of an OR gate 60. The latter collectors are also connected respectively to the Set inputs of a pair of additional flip-flops 59e and 59f.

The testing apparatus of the invention may be controlled through the circuitry just described by any suitable control circuits known in the art. A microprocessor 61, for example, may be programmed to receive signals from the Q output terminals of flip-flops 59a through 59d indicative of the condition of the connector contact receptacles being tested and to generate and transmit to action apparatus or circuitry 62 a signal that one or more connector receptacles are defective. As will be considered more particularly hereinafter, microprocessor 61 may also receive interrupt, start, and stop signals indicating the beginning and end of a testing cycle and the testing of individual connector contact rows, and then clear flip-flops 59 via a clear conductor 63 at those points. With the foregoing description of the organization of one specific connector testing apparatus according to the invention in mind, illustrative operations thereof may now be considered. With carriage 22 in the position shown (FIG. 2), that is, outside of frame 36, a connector to be tested is loaded into recess 21 with its capture cones 24 facing upward as viewed in the figure. At this time, switch 49 (FIG. 4) is operated to energize light emitting diodes 45a through 45f. The light beams thus generated pass unimpeded in channels a through f to energize respectively phototransistors 44a through 44f. The operation of each of the stages is the same, the operation being described in connection with the first stage including phototransistor 44a. The latter element is normally nonconducting and the base of transistor 57a has sufficient positive voltage applied thereto from its connection between potential sources 50 and 55 to maintain transistor 57a normally conducting. As a result, the Set input of flip-flop 59a is effectively at ground potential, leaving the latter in its Clear state. When phototransistor 44a is energized by a light beam from LED 45a, the base of transistor 57a is connected effectively to ground through phototransistor 44a thereby cutting off the former. As a result, the Set input of flip-flop 59a rises, due to its now direct connection to positive potential 50, to its high input level to switch flip-flop 59a to its Set state. Its Q output, as a result, transmits a "1" bit to microprocessor 61. Thus, when switch 49 is closed, as mentioned, the foregoing conditions will obtain for each of the stages identified with channels a through f since, with carriage 22 not yet brought within test frame 36, the light beams in all of the channels will be unimpeded. The apparatus of the invention at this time is prepared to begin a detection cycle of operation.

Microprocessor 61 may conveniently be programmed to perform routines for the detection of the aforementioned steady state conditions, the recognition that a cycle of operation is about to start, and the reception of the actual test data and for responding to the information received during these routines. During the steady state conditions of the flip-flops as described in the foregoing, the high inputs being applied to flip-flops 59e and 59f are also applied to the inputs of OR gate 60. As a result, an interrupt signal is generated by the latter element and transmitted to microprocessor 61 which responds by applying a clear signal to conductor 63 to attempt the reset of flip-flops 59a through 59f. The Q outputs of the latter circuits are now read which reading detects the fact that these outputs are still present on each. An interrupt signal is accordingly still present and the routine is repeated, typically, every 20 microseconds until the flip-flops are cleared at which time microprocessor 61 performs its start routine.

This routine is initiated when carriage 22 is moved within detection frame 36 at which time only apertures 34 and 35 present open channels for the light beams. As a result, only flip-flops 59e and 59f are set, the same setting voltages causing OR gate 60 to generate again an interrupt signal. As a result, flip-flops 59a through 59f are cleared and their Q outputs detected to determine the logic states of the channels as $\bar{a}\cdot\bar{b}\cdot\bar{c}\cdot\bar{d}\cdot e\cdot f$. Microprocessor 61 now waits until the interrupt signal is terminated and repeats a reading of the flip-flops to confirm the previous channel logic states and thereby, the fact that the next routine performed will be the detection of data regarding the proper fitting of the connector 20 contacts.

As the first row of apertures 24 appears between frame 36, a first of indexing apertures 33 in channel e provides an unimpeded path for a light beam in that channel although channel f will now be closed. As a result, flip-flop 59e will be set and OR gate 60 will again generate an interrupt signal. The flip-flops are again cleared as a result and read by microprocessor 61 to detect the flip-flop logic states e f indicating that data is now being received from flip-flops 59a through 59d and the interrupt signal is terminated. The Q outputs of the flip-flops are again read to confirm the previous readings of their logic states which, if all of the contacts of the connector row under test are properly fitted, would be a·b·c·d·e·f. As carriage 22 continues its movement within frame 36, the data receiving routine of microprocessor 61 is repeated row by row of connector 20 apertures 24, the logic states e·f of flip-flops 59e and 59f indicating that contact data is being received. After the last row of apertures 24 passes the light beams, the next movement of carriage 22 presents an unimpeded path for a light beam only through aperture 35' in channel f. Flip-flop 59f alone is now set and an interrupt signal is generated by OR gate 60. As a result, a clear signal is applied to conductor 63 to; clear flip-floip 59f, the channel logic states $\bar{a}\cdot\bar{b}\cdot\bar{c}\cdot\bar{d}\cdot\bar{e}\cdot f$ now indicating that a detection cycle has ended.

If during the afore-described data receiving routine, had any one or more of the contact receptacles of any of the connector rows been improperly fitted as shown in FIG. 1 in connection with receptacle 17, the light beam from the corresponding LED 45 would have been obstructed. As a result, one or more of the Q output bits from flip-flops 59a through 59d at the particular row test would be absent. In response to this failure to set one or more of the latter flip-flops, micrprocessor 61 controls the transmission of a defect signal to action apparatus 62 for appropriate action in the detection of a defective connector. This action may comprise a number of operations devisable by one skilled in the art. Apparatus 62, for example, may simply comprise an alarm for alerting the operator of the defective connector. Apparatus 62 could comprise additional mechanisms for ejecting a defective connector from carriage 22 or for marking the connector as defective. If a mechanism of the latter character is employed, the specific row in which the defect occurs may advantageously be so marked in view of the identification of the rows by light beams through carriage 22 indexing apertures 33. The manner in which carriage 22 is caused to move along rails 30 and 31 within frame 36 was not specifically considered in the foregoing description as not constituting an essential element of the invention. As implied in FIG. 2, this carriage movement may be accomplished manually. On the other hand, mechanisms may be readily devised which move carriage 22 under the control of microprocessor 61.

Testing apparatus according to the invention was described in the foregoing for testing a connector having ten rows of four contacts each. It will be appreciated that connectors having more or fewer rows with different members of contacts in each row may be tested by the apparatus of the invention. More broadly, testing apparatus embodying the principles of the invention may be devised to test devices of any character which in their completed form must have clear multiple channels therethrough and it is to be understood that the apparatus of the invention is not limited to the testing of the illustrative electrical connector as described, the scope of the invention being limited only as defined in the accompanying claims.

What is claimed is:

1. Apparatus for testing an electrical connector (20) having a plurality of rows (23) of terminal pin receptacles (16, 17) characterized in a carriage (22) having a base (25) for supporting said connector (20), said base (25) having a plurality of rows of apertures (33') corresponding to said plurality of rows (23) of receptacles (16), a row of first light emitting devices (45a-45d) and a row of first light sensing devices (44a-44d), each row corresponding to said rows of apertures (33'), said first light emitting devices and said first light sensing devices being spaced apart to permit movement of said carriage (22) and said connector (20) therebetween, said first light sensing devices generating output signals responsive to light passing uninterruptedly from said first light emitting devices through said receptacles (16) when said rows (23) of receptacles of said connector (20) are moved between said row of first light emitting devices and said row of first light sensing devices, and further characterized in that said base (25) has a first additional aperture (33) for each of said rows of apertures (33') and in that a second light sensing device (44e) and a second light emitting device (45e) is added, respectively, to said rows of first light sensing devices (44a-44d) and first light emitting devices (45a-45d), said second light sensing device (44e) generating signals responsive to light passing from said second light emitting device (45e) through said first additional apertures (33) indicating the alignment of said rows (23) of receptacles of said connector (20) between said rows of first light emitting devices and first light sensing devices.

2. Apparatus for testing an electrical connector having a plurality of rows (23) of terminal pin receptacles (16, 17) characterized in a carriage (22) for supporting said connector (20), said carriage (22) presenting unimpeded light paths therethrough, a frame (36) having a first and a second substantially parallel member (40, 41), a row of first light emitting devices (45a-45e) carried by said second member (41) and a row of first light sensing devices (44a-44d) carried by said first member (40), each row corresponding to said plurality of rows (23) of receptacles (16, 17), said first light emitting devices and light sensing devices being spaced apart to permit movement of said carriage (22) and said connector (20) therebetween, said first light sensing devices (44a-44d) generating output signals responsive to light passing from said first light emitting devices through said receptacles (16) when said receptacles are unobstructed when said rows (23) of said receptacles are moved between said row of first light emitting devices and said row of first light sensing devices, and further characterized in rail means (30, 31) extending through said frame (36) and in that said carriage (22) is adapted for slidable movement on said rail means, and in that said carriage (22) is provided with a plurality of indexing apertures (33) corresponding to said rows (23) of receptacles (16, 17) and in that a second light emitting device (45e) and a second light sensing device (44e) are carried by said second and first members (41, 40), respectively, said second light sensing device (44e) generating indexing signals responsive to light passing from said second light emitting device (45e) through said plurality of indexing apertures (33) when said rows (23) of said receptacles are moved between said first light emitting and sensing devices (45a-45d, 44a-44d) for indicating the alignment of said rows of said receptacles.

3. Apparatus as claimed in claim 1 further characterized in that said base (25) has a second additional aperture (35) preceding said first additional apertures (33), and in that a third light sensing device (44f) and a third light emitting device (45f) is added, respectively, to said rows of first light sensing devices (44a-44d) and first light emitting devices (45a-45d), said third light sensing device (44f) generating signals responsive to light passing from said third light emitting device (45f) through said second additional aperture (35) indicating the initiation of a testing cycle.

4. Apparatus as claimed in claim 3 further characterized in that said base (25) has a third additional aperture (35') following said first additional apertures (33), said third light sensing device (44f) generating signals responsive to light passing from said third light emitting device (45f) through said third additional aperture (35') indicating the termination of a testing cycle.

5. Apparatus as claimed in claim 3, 4, or 1 further characterized in that each of said light emitting devices (45) comprises a light emitting diode.

6. Apparatus as claimed in claim 3, 4, or 1 further characterized in that each of said light sensing devices (44) comprises a phototransistor.

7. Apparatus as claimed in claim 1 further characterized in circuit means (FIG. 4) energized responsive to the absence of said output signals when said rows (23) of receptacles of said connector (20) are moved between said row of first light emitting devices (45a-45d) and said row of first light sensing devices (44a-44d) for generating defect signals.

8. Apparatus for testing an article of manufacture (20) having at least one channel therethrough characterized in a carriage (22) for supporting said article (20), said carriage being formed to present an unimpeded light path therethrough at said channel, a first light emitting device (45a) and a first light sensing device (44a), said devices (45a, 44a) being spaced apart to permit movement of said carriage (22) and said article (20) therebetween, said light sensing device (44a) generating output signals responsive to light passing uninterruptedly from said light emitting device (45a) through said channel when said carriage (22) is moved between said light emitting and sensing devices (45a, 44a), further characterized in that said carriage (22) has an aperture (33) therethrough aligned with said channel when said article (20) is supported by said carriage (22) and in a second light emitting device (45e) and a second light sensing device (44e) for generating an indexing signal responsive to light passing from said second light emitting device (45e) through said aperture (33) indicating an alignment of said channel, and further characterized in rail means (30, 31) and in that said carriage (22) is adapted for slidable movement on said rail means.

* * * * *